United States Patent
Yoshizaki

(10) Patent No.: US 11,083,701 B2
(45) Date of Patent: Aug. 10, 2021

(54) DERMATOMYCOSIS TREATMENT AGENT

(71) Applicant: Shiro Yoshizaki, Tokushima (JP)

(72) Inventor: Shiro Yoshizaki, Tokushima (JP)

( * ) Notice: Subject to any disclaimer, the term of this patent is extended or adjusted under 35 U.S.C. 154(b) by 61 days.

(21) Appl. No.: 15/740,523

(22) PCT Filed: Jun. 20, 2016

(86) PCT No.: PCT/JP2016/068205
§ 371 (c)(1),
(2) Date: Dec. 28, 2017

(87) PCT Pub. No.: WO2017/018094
PCT Pub. Date: Feb. 2, 2017

(65) Prior Publication Data
US 2018/0207115 A1 Jul. 26, 2018

(30) Foreign Application Priority Data
Jul. 24, 2015 (JP) .............................. JP2015-146556

(51) Int. Cl.
*A61K 31/194* (2006.01)
*A61P 17/00* (2006.01)
*A61P 31/10* (2006.01)
*A61K 9/00* (2006.01)
*A61K 9/08* (2006.01)

(52) U.S. Cl.
CPC .......... *A61K 31/194* (2013.01); *A61K 9/0014* (2013.01); *A61K 9/08* (2013.01); *A61P 17/00* (2018.01); *A61P 31/10* (2018.01)

(58) Field of Classification Search
CPC ...... A61K 31/194; A61K 9/0014; A61P 17/00
See application file for complete search history.

(56) References Cited

U.S. PATENT DOCUMENTS

2015/0196520 A1   7/2015   Yoshizaki

FOREIGN PATENT DOCUMENTS

| JP | H3-200730 | | 9/1991 |
|---|---|---|---|
| JP | H4-149129 | | 5/1992 |
| JP | H4-76973 | | 12/1992 |
| JP | H9-194373 | * | 7/1997 |
| JP | 3120965 | | 12/2000 |
| JP | 2003-144535 | | 5/2003 |
| JP | 2003-171304 | | 6/2003 |
| JP | 3628647 | | 3/2005 |
| JP | 2005-255638 | | 9/2005 |
| JP | 2005-263695 | * | 9/2005 |
| JP | 2007-063227 | | 3/2007 |
| JP | 2012-526727 | | 11/2012 |
| JP | 5548832 | | 7/2014 |
| WO | WO-2004/010952 A2 | | 2/2004 |
| WO | WO 2010/130028 | * | 11/2010 |
| WO | WO 2020/130028 | * | 11/2010 |
| WO | WO 2014/045961 | * | 3/2014 |
| WO | WO-2014045961 A1 | * | 3/2014 ........... A61K 9/0014 |

OTHER PUBLICATIONS

Osada et. al. (Nitto Shoin, Japan (2005). (Year: 2005).*
Bastin et. al. (Organic Process Research and Development (2000) 4:427-435). (Year: 2000).*
Davidson, "Chemical Preservatives and Natural Antimicrobial Compounds" Food Microbiology Fundamentals and Frontiers, 1997, pp. 521-523.
Foley, et al., "Studies on the effect of pH and solubility on the anti-fungal properties of fatty acids, trimethyl cetyl ammonium pentachlorophenate and other agents", Journal of Investigative Dermatology, 1948, vol. 10, pp. 249-263.
Lee, et al., "Antibacterial Activity of Citrate and Acetate", Nutrition, vol. 18, pp. 665-666, 2002.
Matsuda, et al., "Antimicrobial Activities of Organic Acids Determined by Minimum Inhibitory Concentrations at Different pH Ranged from 4.0 to 7.0", Nippon Shokuhin Kogyo Gakkaishi, vol. 41, No. 10, 687-702 (1994).
Office Action issued in JP 2015-146556.
Osada,et al., "Citric Acid Keeps the Doctor Away", Nitto Shoin, 2005, p. 114.
Sullivan, et al., "Study of nutritional requirements of Trichophyton tonsurans", Arch Dermatol and Syphilol, 1954, vol. 70, No. 1, pp. 84-90.
Szyndel, et al., "In vitro effects of acetates, sodium ascorbate, sodium citrate and sodium silicate salts on radical growth of several phytopathogenic fungi", Phytopatholoty, 2000, vol. 90, No. 6, Supplement.
Targeted Control of Microorganisms Toxic to Food, 2009, pp. 31-41.pdf.
Balestrino et al "Eradication of Microorganisms Embedded in Biofilm by an Ethanol-Based Catheter Lock Solution" Nephrology Dialysis Transplantation vol. 24, pp. 3204-3209, 2009.
Ely et al "Diagnosis and Management of Tinea Infections" American Family Physician vol. 90, pp. 702-710, 2014.
Regev-Shoshani et al "A Nitric Oxide-Releasing Solution as a Potential Treatment for Fungi Associated with Tinea Pedis" Journal of Applied Microbiology vol. 114, pp. 536-544, 2012.
Extended European Search Report issued in EP 16 830 199.2.

* cited by examiner

*Primary Examiner* — Marcos L Sznaidman
(74) *Attorney, Agent, or Firm* — Cesari & McKenna, LLP

(57) ABSTRACT

Provided is a means effective in treating dermatomycosis. An external therapeutic agent for treating dermatomycosis containing a trialkali metal salt of citric acid.

3 Claims, No Drawings

DERMATOMYCOSIS TREATMENT AGENT

CROSS REFERENCE TO RELATED APPLICATIONS

This application is the National Stage of International Application No. PCT/JP2016/068205, filed on Jun. 20, 2016, which claims priority to Japanese Application No. 2015-146556, filed on Jul. 24, 2015. The contents of both applications are hereby incorporated by reference in their entirety.

TECHNICAL FIELD

The present invention relates to a therapeutic agent for dermatomycosis.

BACKGROUND ART

Organic acids (carboxylic acids) are known to exhibit antimicrobial activity against a variety of microorganisms, and some carboxylic acids have been widely used as preservatives for food, for example. Several carboxylic acids are also known to have a curative action on dermatomycosis caused by pathogenic fungi, such as dermatophytic fungi ("tinea"). However, it is relatively unknown that salts of carboxylic acids have antimicrobial activity against pathogenic fungi.

There has been no publicly disclosed patent document that clearly states that citric acid alone has a therapeutic action on dermatophytosis, regarding the association of citric acid with tinea. Only a few patent documents disclose that a mixture of other antimicrobial active substances with citric acid exhibits a curative action on tinea. For example, the following are reported: a mixture of horse oil having antimicrobial activity with 15% citric acid (Patent Literature 1); a mixture of a bamboo vinegar solution, which is a folk medicine for tinea, with 1% citric acid (Patent Literature 2 and 3); a mixture of a fermented liquid of *Alpinia speciosa* extract with *moromizu* vinegar, which contains citric acid (Patent Literature 4); a mixture of *tororo aoi* extract, salicylic acid, and citric acid (Patent Literature 5); a tinea transmission-preventing product obtained by mixing seawater salt, citric acid, and other components (Patent Literature 6); and a citric acid-containing film preparation for treating tinea (Patent Literature 7).

The following two patent documents mention the association of citric acid salts with tinea. It is disclosed that adding an adjuvant (sodium citrate, bismuth gallate, bismuth subnitrate) to bifonazole, which is a known tinea medicine, increases the antimicrobial activity of bifonazole (Patent Literature 8, 9). However, why the antifungal activity of bifonazole is increased by these adjuvants remains unknown, and the role of sodium citrate as an adjuvant has yet to be elucidated. Additionally, a product of Shiseido Japan Co., Ltd., eau de cologne massage gel, "Qiora Inner Serum R (dispenser type)" is said to cure tinea of a tinea patient, and a mixture containing all of the 11 components of this product is disclosed as a therapeutic medicine for tinea (Patent Literature 10). Although sodium citrate is contained as one of these components, which component of these 11 components exhibits a tinea curative action remains unknown, and has not been elucidated. A patent document that mentions the association of carboxylic acid salts with tinea discloses that external application of alkali metal salts (sodium salts or potassium salts) of benzoic acid, sorbic acid, or edetic acid can cure intractable tinea, such as tinea unguium and hyperkeratotic tinea (Patent Literature 11).

The main factor of why carboxylic acids exhibit antimicrobial activity includes a decrease in pH attributed to the acidity of carboxylic acids. Additionally, disturbance inside a microorganism caused by the pH decrease, which is due to incorporation of a unionized, undissociated carboxylic acid into the body of the microorganism, and effects inherent to carboxylic acids are also considered to be factors of antimicrobial activity (Non-patent Literature 1). Carboxylic acids used as a tinea medicine include acetic acids (vinegar, pyroligneous acid solution, bamboo vinegar solution) that are folk medicines and Kadako, which is a Chinese tinea medicine (containing benzoic acid and salicylic acid). Citric acid is also known as a folk medicine (Non-patent Literature 2). However, some academic papers report that citric acid does not show antimicrobial activity against fungi. Matsuda et al., report that citric acid and trisodium citrate did not exhibit antimicrobial activity against *Candida* (*Candida krusei*) and *Aspergillus* (*Aspergillus oryzae*), which are pathogenic fungi (Non-patent Literature 3). Carboxylic acids approved as an antifungal medicine in Japan (therapeutic medicine for tinea) include undecylenic acid having 11 carbon atoms; however, this is hardly used in clinical practice (Non-patent Literature 4). Although an academic paper states that trisodium citrate exhibited antimicrobial activity against *Candida* (*Candida albicans*), its MIC value is several tens of thousands times or more weaker than the MIC value of a synthetic antimicrobial agent that is clinically used against candidiasis, and its actual efficacy for candidiasis is not shown (Non-patent Literature 5). As noted above, the antimicrobial activity of carboxylic acids is considered to be attributable to undissociated carboxylic acid molecules; thus, carboxylic acid salts are regarded as not having antimicrobial activity. Additionally, a carboxylic acid anion generated by dissociation of a carboxylic acid salt is assumed to not pass through the cell wall of a microorganism; thus, carboxylic acid salts are believed to not have antimicrobial activity.

CITATION LIST

Patent Literature

Patent Literature 1: JP1992-149129A
Patent Literature 2: JP2003-171304A
Patent Literature 3: U.S. Pat. No. 3,628,647
Patent Literature 4: JP2005-255638A
Patent Literature 5: JP1992-76973A
Patent Literature 6: JP2003-144535A
Patent Literature 7: JP2007-63227A
Patent Literature 8: JP1997-194373A
Patent Literature 9: U.S. Pat. No. 3,120,965
Patent Literature 10: JP2005-263695A
Patent Literature 11: U.S. Pat. No. 5,548,832

Non-Patent Literature

Non-patent Literature 1: *Shokuhin Kigai Biseibutsu no Target Seigyo*, p. 33, Toshio MATSUDA, Saiwaishobo, 2009.
Non-patent Literature 2: *Kuen San de Isha Irazu*, p. 114, Shomatsu OSADA, Toru KOJIMA, Nitto Shoin, 2005.
Non-patent Literature 3: Antimicrobial Activities of Organic Acids Determined by Minimum Inhibitory Concentrations at Different pH Ranged from 4.0 to 7.0, Toshio MATSUDA, Toshihiro YANO, Akihiro MARUYAMA, Hidehiko KUMAGAI, Journal of Food Science and Technology, 41, 687 (1994).

Non-patent Literature 4: E. J. Foley and S. W. Lee, J. Invest. Dermatol., 10, 249 (1948).

Non-patent Literature 5: Yee-Lean Lee, T. Cesario, J. Owens, E. Shanbrom, and L. D. Thrupp, Nutrition, 18, 665-666 (2002).

SUMMARY OF INVENTION

Technical Problem

Tinea in humans or other animals is a zoonotic disease, and is known for being difficult to completely cure by drug treatment. It is unknown why tinea fungi parasitic to the shallow part of the skin cannot be killed. A major consideration is that synthetic antifungal agents, such as azole-based antifungal agents or allyl amine-based antifungal agents, used in the field of dermatology are less likely to penetrate into the skin. Although these antifungal agents show potent antimicrobial activity against dermatophytic fungi in an in vitro drug-sensitivity test, tinea cannot be cured unless the medicinal agents reach the site where a dermatophytic fungus is present. This requires the development of novel types of medicinal agent excellent in permeability into the skin as a new tinea medicine, and a medicinal agent having such skin permeability is expected to have a potency to cure tinea. Tinea unguium is treated with an internally applied antifungal agent. However, this internal remedy may be accompanied by side effects including liver damage, and there is demand for the development of externally applied medicinal agents that can cure tinea unguium with fewer side effects. Specifically, an object of the present invention is to provide therapeutic agents for dermatomycosis that penetrate through the skin or nails in an excellent manner, and that can effectively treat dermatophytosis etc.

Solution to Problem

To achieve the object, research on antifungal agents must be performed from perspectives completely different from traditionally used methods, by which analogs of synthetic antifungal agents have been studied. Traditional synthetic antifungal agents are typically insoluble or poorly soluble in water, and this appears to be the major factor for losing permeability into the skin. To increase the permeability, selecting compounds with high water solubility is desired. Making investigation on the basis of this concept, the present inventor found that an alkali metal salt of benzoic acid, sorbic acid, or edetic acid exhibits an excellent tinea curative effect (Patent Literature 11). The inventor conducted further research, and found that trialkali metal salts of citric acid have an excellent tinea curative effect without skin irritation. The inventor conducted further research based on these findings, and completed the present invention including the following subject matter.

Item 1.
An external therapeutic agent for treating dermatomycosis comprising a trialkali metal salt of citric acid.

Item 2.
The external therapeutic agent for treating dermatomycosis according to Item 1, wherein the trialkali metal salt of citric acid is tripotassium citrate or trisodium citrate.

Item 3.
The external therapeutic agent for treating dermatomycosis according to Item 1 or 2, which is in the form of fluid.

Item 4.
The external therapeutic agent for treating dermatomycosis according to Item 3, wherein an area affected by dermatomycosis is immersed in the fluid.

Advantageous Effects of Invention

Citric acid greatly irritates the skin due to its acidity, and is thus hard to use for treating human tinea. Trialkali metal salts of citric acid, however, are gentler to the skin because of the absence of acidity, and can be safely used as a tinea therapeutic agent. Because citric acid is one of the component substances of the citric acid cycle, which is the most important biochemical reaction pathway associated with aerobic metabolism, and is abundant in the human body, citric acid is highly safe. Trialkali metal salts of citric acid contribute to the betterment of life for mankind as an ideal tinea therapeutic medicine, exhibiting a potent curative action against dermatomycosis with fewer side effects.

DESCRIPTION OF EMBODIMENTS

Trialkali metal salts of citric acid include tripotassium citrate and trisodium citrate. Both of these trialkali metal salts of citric acid have been found to be capable of easily curing human tinea when externally applied. Specifically, a trialkali metal salt of citric acid dissociates into three anions in the presence of water, and the three anions easily penetrate into the skin of the area affected by dermatomycosis. Because the three anions of citric acid exhibit an excellent tinea curative effect, it is clear that the three anions of citric acid have action on pathogenic fungi, such as dermatophytic fungi, through an unknown mechanism, which is completely different from the traditionally assumed antimicrobial action mechanism, in which the acidity attributable to carboxylic acid is believed to exhibit antimicrobial activity. This unknown antimicrobial activity of three anions of citric acid appears to be achieved because the chelate effect of the three anions of citric acid deprives pathogenic fungi of metal ions that play a crucial part (e.g., calcium ions, magnesium ions, zinc ions, and iron ions), rendering the fungi unable to survive. Ions are typically considered to not permeate through the skin. However, the horny layer barrier of the area affected by dermatomycosis is destroyed by fungi; thus, citric acid anions appear to migrate into the skin horny layer.

Aqueous solutions of trialkali metal salts of citric acid penetrate well through the skin or nails, and easily and completely cure tinea, which has thus far been considered difficult to treat. In the case of skin tinea, applying a medicinal agent containing a trialkali metal salt of citric acid onto the area affected by tinea, for example, 1 to 3 times daily maintains the concentration of the medicinal agent necessary for killing the pathogenic fungus inside the skin to eliminate the fungus, thereby completely curing tinea in a 1-week to several-month treatment.

Aqueous solutions of trialkali metal salts of citric acid also penetrate well through nail tissue, and can cure tinea unguium when externally applied. In the case of tinea unguium, applying a medicinal agent containing a trialkali metal salt of citric acid onto the affected area of a nail 1 to 3 times daily maintains the concentration of the medicinal agent necessary for killing the pathogenic fungus inside the affected area to eliminate the fungus, thereby completely curing tinea unguium in a treatment of several months to one and a half years. Nail tissue grows slowly, and it takes about 3 months until a new fingernail replaces the old nail, and a half year to one year or more until a new toenail replaces the old nail. Thus, tinea unguium requires long-term treatment. To cure tinea unguium, it is desirable to kill the pathogenic fungus in the innermost area of the affected area of the nail. To do this, it is effective to immerse the entire nail for a long time in a fluid agent containing a trialkali metal salt of citric acid, which can effectively sterilize and eliminate the pathogenic fungus present inside the nail. Performing this nail immersion treatment once daily for 1 to 5 hours or during sleep hours, about 1 to 10 times in succession, eliminates the pathogenic fungus in the nail. After the treatment, a new nail grows over time, recovering a healthy nail. It is often the case for tinea unguium that fungal infection also develops in the skin around the nail; thus, it is preferable to continue, for several months, the treatment of immersing the entire nail in a fluid agent.

Thus far, tinea unguium has only been cured by an internal remedy using an internally applied antifungal medicine. However, the use of a fluid agent containing a trialkali metal salt of citric acid has been found to be capable of curing tinea unguium in an external remedy. Trialkali metal salts of citric acid have a near-neutral pH, with less irritation on the skin caused by acidity of citric acid; thus, trialkali metal salts of citric acid also have excellent properties in the low likelihood of developing skin inflammation. As noted above, trialkali metal salts of citric acid will contribute to the betterment of life for mankind as an ideal therapeutic agent for dermatomycosis ("tinea").

The medicinal agent concentration of a trialkali metal salt of citric acid for use in an external therapeutic agent can be selected from the range within which pathogenic fungi, such as dermatophytic fungi, can be killed. It is also preferable to maintain the concentration for a long time after three anions of citric acid has permeated into the skin. Additionally, it is preferable in the case of tinea unguium that three anions of citric acid reach the innermost area of a nail inhabited by fungi. From this standpoint, the concentration of a trialkali metal salt of citric acid is preferably about 0.1 to 20 wt %, and more preferably 0.5 to 10 wt %. An excessively low medicinal agent concentration requires more frequent administration of the medicinal agent due to its insufficient effect on dermatophytic fungi. An excessively high medicinal agent concentration irritates the skin to a greater degree, possibly causing inflammation in sensitive parts of the skin.

Trialkali metal salts of citric acid are sufficiently water-soluble for use in drugs. Thus, dosage forms, such as fluids, cream, spray, and ointment, can suitably be selected for trialkali metal salts of citric acid as necessary. The solvent for dissolving an alkali metal salt of citric acid for use includes any solvent that can dissolve a citric acid salt, such as water, ethanol, isopropanol, glycerin, ethylene glycol, propylene glycol, and macrogol. An alkali metal salt of citric acid may be used in combination with a known synthetic antifungal medicine; an alkali metal salt of citric acid may also be mixed with a folk medicine for tinea, such as pyroligneous acid solutions, bamboo vinegar solutions, acetic acid, and plant extracts, in any proportions. It is, however, preferable to not use these known medicinal agents in combination, because they are highly irritating to the skin.

The antimicrobial activity of therapeutic agents for treating dermatomycosis was evaluated and confirmed by performing a drug-sensitivity test with major pathogenic fungi in accordance with the CLSI (Clinical Laboratory Standards Institute, U.S.) guidelines. The pathogenic fungi selected were genus *Trichophyton* (*T. rubrum*, *T. mentagrophytes*), genus *Microsporum* (*M. gypseum*), genus *Epidermophyton* (*E. floccosum*), genus *Candida* (*C. albicans*), genus *Aspergillus* (*A. fumigatus*), and genus *Cryptococcus* (*C. neoformans*). The Examples show the test results. The antimicrobial activity of the compounds of the present invention (MIC, mg/ml) against *T. mentagrophytes*, which is a typical dermatophytic fungus, is as follows: tripotassium citrate 3.1; and trisodium citrate 6.3. A drug-sensitivity test with a fungus belonging to genus *Malassezia* (*M. furfur*) was also performed in accordance with the method of Sugita et al., which employs an agar dilution method (T. Sugita et al., J. Clinical Microbiology, 43, 2824-2829 (2005)). The antimicrobial activity against *M. furfur* (MIC, mg/ml) was as follows: tripotassium citrate 10.0.

In these drug-sensitivity tests, the medium contained Mg ions and Ca ions necessary for fungal conidia (spores) to germinate and grow. Because carboxyl groups of organic acids bind to these ions, organic acids have competitive inhibitory activity on fungal growth. Trialkali metal salts of citric acid appear to firmly bind to these ions and exhibit antimicrobial activity, inhibiting fungal growth by removing these ions from the test system. This finding that citric acid salts, capable of firmly binding to magnesium ions and calcium ions, exhibit antimicrobial activity against fungi defies the conventional wisdom that undissociated organic acids exhibit antimicrobial activity.

Because trialkali metal salts of citric acid exhibit antimicrobial activity by binding primarily to Mg ions and Ca ions, trialkali metal salts of citric acid exhibit effective antimicrobial activity inside the skin horny layer in which these ions are less likely supplied from blood. Both dihydrogen citrate monoalkali metal salts and monohydrogen citrate dialkali metal salts also have antimicrobial activity against pathogenic fungi; however, these salts irritate the skin due to the free carboxyl groups contained therein, and have a relatively lower tinea curative effect. Alkali metal salts of isocitric acid, which is one component substance of the citric acid cycle, also exhibit antimicrobial activity against pathogenic fungi.

In the antimicrobial activity measurement method in accordance with the CLSI guidelines described above, an excessively large amount of magnesium ions and calcium ions is added to the RPMI-1640 medium for use. Thus, the trialkali metal salt of citric acid added to the test system binds completely to the excessively large amount of metal ions, resulting in an apparently large MIC value. For this reason, the ICP analytical method was performed to measure the content of magnesium ions and calcium ions in a test solution used as a blank test in this test system (a solution obtained by adding a solution containing spores of *T. mentagrophytes* to a RPMI-1640 medium solution, and performing a culture treatment) and to measure the content of magnesium ions and calcium ions in the original RPMI-1640 medium solution, thereby calculating the amount of alkali metal ions absorbed by the spores of *T. mentagrophytes*. The amount of the citric salt that can bind to all of the alkali metal ions absorbed by the spores is the substantial MIC value. The corrected MIC value of tripotassium citrate against *T. mentagrophytes* (mg/ml) was 0.054.

The curative action of trialkali metal salts of citric acid on dermatomycosis was determined based on whether there was a therapeutic effect on human tinea. The cases of tinea used in the test include a variety of cases, such as vesicular tinea on the skin, interdigital tinea, hyperkeratotic tinea, tinea corporis, and tinea unguium. As shown in Examples 3 to 13, medicinal agents containing a trialkali metal salt of citric acid exhibited an excellent effect, readily curing tinea on the skin, and also cured tinea unguium in external remedies. In these cases, no skin irritation due to the medicinal agents was confirmed. In many cases described in the Examples, *Trichophyton* fungus was isolated and identified as a pathogenic fungus; additionally, Example 10 describes a case in which *Candida* was isolated and identified, and Example 11 describes a case in which *Aspergillus* was isolated and identified. To date, it has been completely unknown that a substance containing a trialkali metal salt of citric acid can cure dermatomycosis, such as dermatophytosis; the present invention has revealed this for the first time.

Over the course of investigation into the curative action of trialkali metal salts of citric acid on human tinea, trialkali metal salts of citric acid were found to be capable of causing the fungal spores present underneath the skin to germinate. Applying a 5% tripotassium citrate solution on the small red papules on the body made the papules smooth, and relapse of symptoms was observed after every day, with development of pigmentation, and followed by complete cure; this phenomenon was observed quite frequently. The relapse of symptoms was caused by germination of spores, and tripotassium citrate appears to have induced the germination of spores. The biggest factor for the low likelihood of curing dermatomycosis is the presence of spores; even after a treatment with a medicinal agent, if spores remain, the spores germinate, enabling dermatomycosis to return. Because trialkali metal salts of citric acid allow spores to germinate and then efficiently kill them, trialkali metal salts of citric acid are considered to serve as an ideal therapeutic agent for treating dermatomycosis. Thus far, no medicinal agents have been known for the action of allowing spores underneath the skin to germinate.

EXAMPLES

The following describes the present invention in more detail. However, the present invention is not limited to these Examples.

Example 1

The antifungal activity of tripotassium citrate and trisodium citrate against a variety of pathogenic fungi was evaluated by performing a drug-sensitivity test. The test was performed using a microdilution method in accordance with the CLSI (Clinical Laboratory Standards Institute, U.S.) guidelines. The antimicrobial activity of tripotassium citrate against various pathogenic fungi is shown below with the name of each fungus, the fungus number, and MIC (mg/ml).
*T. rubrum*, IFM59814, 12.5
*T. mentagrophytes*, IFM59813, 3.1
*M. gypseum*, IFM58916, 12.5
*E. floccosum*, IFM53345, 1.6;
*C. albicans*, IFM5740, 25
*A. fumigatus*, IFM4942, 6.3
*C. neoformans*, IFM5807, 0.39

The antimicrobial activity of trisodium citrate against *T. mentagrophytes* IFM59813 was 6.3 (MIC, mg/ml). The antimicrobial activity of amphotericin B, which was a control drug, against *T. mentagrophytes* IFM59813 was 2.0 (MIC, mg/ml). The MIC value (mg/ml) of tripotassium citrate, obtained by measuring and correcting the amount of alkali metal ions absorbed by spores of *T. mentagrophytes* IFM59813, was 0.054.

Example 2

The antimicrobial activity of tripotassium citrate against fungi belonging to genus *Malassezia* was evaluated by performing a drug-sensitivity test with human-related *Malassezia* species, in accordance with the method disclosed in Sugita et al. (2005). The test drug and mLNA medium was added to each well of a 24-well microtiter plate to give 2 mL in total. 50 μL of a microbe suspension with a concentration of about $1 \times 10^4$ cell/ml was added to the medium, and aerobically cultured at 32° C. for 7 days. The concentration at which growth was completely inhibited, compared with the control (no test drug added), was determined to be a minimum inhibitory concentration (MIC). The antimicrobial activity of tripotassium citrate against *M. furfur* was 10.0 (MIC value, mg/ml).

Example 3

20% ethanol was added to 5.3 g of tripotassium citrate monohydrate to give 1000 g, thereby preparing a 0.5% test solution. The 0.5% test solution was applied to hyperkeratotic tinea that extensively developed on the arch on the sole of a foot by spraying the solution three times daily. After about 3 months of treatment, the intractable, recurring hyperkeratotic tinea disappeared, and clean skin grew back. From the area affected by this tinea, *Trichophyton mentagrophytes*, which is one type of *Trichophyton* fungi, was isolated and confirmed.

Example 4

20 mL of glycerin (84-87% aqueous solution) was added to 63.6 g of tripotassium citrate monohydrate, and 15% ethanol was further added thereto to give 2 L, thereby preparing a 3% test solution. This 3% test solution was applied twice daily, by spraying the solution, to vesicular tinea that extensively developed on the arch of the left foot. After about 1 month, the skin symptom practically disappeared. After the treatment was further continued for about 1 month, this tinea was cured.

Example 5

A 3% test solution of tripotassium citrate prepared in the same manner as in Example 4 was sprayed twice daily onto tinea corporis that extensively developed over the left part of the buttocks. After about 2 months, tinea corporis disappeared, and healthy skin grew back. Although light brown pigmentation developed on the healed skin, it faded away over time and became less prominent.

Example 6

A 3% test solution prepared in the same manner as in Example 4 was sprayed once daily onto thin hyperkeratotic tinea that extensively developed over around the tip of the nails on the sole of both feet. The thin hyperkeratotic skin was gradually peeled, and after about 1 month, pink-color, healthy skin grew back. From this affected area of the skin, *Trichophyton rubrum* was isolated and confirmed.

Example 7

A 3% test solution prepared in the same manner as in Example 4 was sprayed once daily onto interdigital tinea that extensively developed between the toes of the feet. After about 2 months, the skin symptom disappeared, and healthy skin grew back.

Example 8

In the case in which tinea developed in all four nails except the fourth nail of the left foot, the entire foot was immersed for 1 hour daily in a 3% test solution prepared in the same manner as in Example 4. Over the course of the treatment, new nails grew from the base of the nails. After a half year, tinea in all of the nails was fully cured, and healthy nails returned.

Example 9

20 mL of glycerin (84-87% aqueous solution) was added to 106 g of tripotassium citrate monohydrate, and 15% ethanol was further added thereto to give 2 L, thereby preparing a 5% test solution. About 2 mL of this test solution was placed into a commercially available fingerstall (size M). The middle finger of the right hand, which developed tinea on the right edge of the nail and the surrounding skin from the tip to the base of the nail, was immersed in the solution for 5 hours once every 2 days. After 3 months of this treatment, a healthy nail and skin grew back. From the nail specimen of this case, a *Trichophyton* fungus was isolated, and confirmed to be *Trichophyton rubrum* by gene analysis.

Example 10

A 5% solution of tripotassium citrate prepared in the same manner as in Example 9 was sufficiently sprayed once daily on tinea unguium on the tip of the nail of the fourth finger of the right hand. After one and a half months, the affected area of the nail shifted toward the nail tip, and was trimmed with a nail clipper; accordingly, tinea unguium was cured. From the nail specimen of this affected area, a *Candida* fungus was isolated and confirmed to be *Clavispora lusitaniae* (the teleomorph of *Candida lusitaniae*) by gene analysis.

Example 11

A 5% solution of tripotassium citrate prepared in the same manner as in Example 9 was sprayed once daily on small red papules that developed on the left chest part. The small red papules on the affected area immediately shrank, and after one week, pigmentation and cicatrization occurred. From the small red papules, a body fluid was collected, and the pathogen was cultured, followed by gene analysis, thereby confirming *Aspergillus tubingensis* as the pathogen.

Example 12

A 10% aqueous solution of tripotassium citrate was prepared. This 10% test solution was sprayed once daily on the right thumbnail, the entirety of which had developed tinea unguium. Over the course of the treatment, a healthy nail grew from the base of the nail, and after a half year, a healthy nail returned.

Example 13

A 3% test solution of trisodium citrate was prepared in the same manner as in Example 4. This 5% test solution was sprayed once daily on small red papules that developed on the left thigh. The small red papules on the affected area immediately shrank, and after 2 weeks, cicatrization and pigmentation occurred.

INDUSTRIAL APPLICABILITY

A therapeutic agent is provided for dermatomycosis ("tinea"), which many people in Japan are believed to suffer from. Although tinea has been a hard-to-cure disease, the use of the therapeutic agent for treating dermatomycosis of the present invention can easily cure tinea. Additionally, the use of the therapeutic agent has opened the door to external remedies for curing tinea unguium, which has only been considered treatable by internally applied remedies. Thus, the present invention can relieve mankind from the calamity of tinea, and is thus highly industrially applicable.

The invention claimed is:

1. A method of treating dermatomycosis, comprising topically administering to a subject in need thereof a composition comprising 0.1 to 20 wt % of tripotassium citrate and a pharmaceutically acceptable excipient, wherein the tripotassium citrate is the only component in the composition having antifungal activity.

2. The method according to claim 1, wherein the composition is in the form of a fluid.

3. The method according to claim 2, wherein the topically administering comprises immersing an area affected by dermatomycosis of the subject in the fluid.

* * * * *